US009597688B2

(12) United States Patent
Fischer et al.

(10) Patent No.: US 9,597,688 B2
(45) Date of Patent: Mar. 21, 2017

(54) POLYMER SUBSTRATE WITH FLUORESCENT STRUCTURE, METHOD FOR THE PRODUCTION THEREOF AND THE USE THEREOF

(75) Inventors: Thomas Fischer, Berlin (DE); Joachim Stumpe, Nauen (DE); Valentin Kahl, München (DE)

(73) Assignee: ibidi GmbH, Martinsfied (DE)

( * ) Notice: Subject to any disclaimer, the term of this patent is extended or adjusted under 35 U.S.C. 154(b) by 316 days.

(21) Appl. No.: 12/876,881

(22) Filed: Sep. 7, 2010

(65) Prior Publication Data

US 2011/0086420 A1 Apr. 14, 2011

(30) Foreign Application Priority Data

Sep. 8, 2009 (EP) .................................... 09011507

(51) Int. Cl.
*C12M 1/26* (2006.01)
*C12M 3/00* (2006.01)
(Continued)

(52) U.S. Cl.
CPC .................................... *B01L 3/545* (2013.01)

(58) Field of Classification Search
CPC ........... B01L 3/545; B60K 11/06; B60K 1/04; B60K 2001/005; B60K 2001/0433;
(Continued)

(56) References Cited

U.S. PATENT DOCUMENTS 5,401,960 A * 3/1995 Fisun et al. .................. 250/271
5,971,276 A * 10/1999 Sano et al. ............... 235/462.01
(Continued)

FOREIGN PATENT DOCUMENTS

DE 42 41 663 A1 6/1994
DE 100 04 135 A1 8/2001
(Continued)

OTHER PUBLICATIONS

Baker et al., *Appl. Phys.*, vol. A 57, pp. 543-544 (1993.
(Continued)

*Primary Examiner* — Nathan Bowers
*Assistant Examiner* — Lydia Edwards
(74) *Attorney, Agent, or Firm* — Leydig Voit & Mayer, LTD

(57) ABSTRACT

The invention relates to polymer substrates which are provided with fluorescence features and in which photochemical fluorescence features, i.e. fluorescent structures, are produced by UV irradiation. Thus, fluorophores can be produced in polymer substrates with a low inherent fluorescence by means of suitable UV radiation, which fluorophores display a marked and detectable emission upon being excited with light of a suitable wavelength. If such an irradiation is implemented in a structured manner, emission patterns can be produced in this way in polymer substrates, which emission patterns can be applied for example as recovery grids in fluorescence microscopy. A further application field relates to product authentication which is made possible by the polymer substrates according to the invention provided with fluorescence features.

22 Claims, 2 Drawing Sheets

(51) Int. Cl.
*C12M 1/24* (2006.01)
*B01L 3/00* (2006.01)

(58) Field of Classification Search
CPC .............. B60L 11/1803; B60L 11/1864; B60L 11/1874; B60L 11/1877; B60L 11/1879; B60L 1/003; B60L 2210/10; B60L 2240/545; B60Y 2306/00
USPC ............................................ 435/283.1–309.4
See application file for complete search history.

(56) References Cited

U.S. PATENT DOCUMENTS

| | | | | |
|---|---|---|---|---|
| 2002/0113216 | A1* | 8/2002 | Fujitugu | 250/492.1 |
| 2003/0219903 | A1* | 11/2003 | Wang et al. | 436/37 |
| 2004/0055492 | A1 | 3/2004 | Van Den Elshout et al. | |
| 2005/0019231 | A1 | 1/2005 | Kahl | |
| 2006/0099452 | A1* | 5/2006 | Kobayashi | 428/690 |
| 2007/0015137 | A1 | 1/2007 | Zantl | |
| 2008/0020455 | A1 | 1/2008 | Zantl et al. | |
| 2008/0274493 | A1* | 11/2008 | Quake et al. | 435/29 |
| 2008/0314167 | A1* | 12/2008 | Kahl | 73/864.91 |
| 2010/0186524 | A1* | 7/2010 | Ariessohn et al. | 73/863.22 |

FOREIGN PATENT DOCUMENTS

| | | | |
|---|---|---|---|
| DE | 101 05 711 | A1 | 9/2002 |
| EP | 1 458 483 | | 9/2004 |
| EP | 1 741 487 | A1 | 1/2007 |
| EP | 1 880 764 | A1 | 1/2008 |
| EP | 2 008 715 | A1 | 12/2008 |
| FR | 2 755 902 | A1 | 5/1998 |
| FR | 2 909 922 | A1 | 6/2008 |
| WO | WO 03/101755 | A1 | 12/2003 |
| WO | WO 2004/087795 | A1 | 10/2004 |
| WO | WO 2005/054830 | A1 | 6/2005 |

OTHER PUBLICATIONS

Carlsson et al., *Photooxidation of Polypropylene Films*, vol. 4, No. 2, pp. 179-184 (1971).

Qin et al., *Optoelectronics Letters*, vol. 4, No. 1, pp. 23-25 (2008).

Office Action in European Appl. No. 09011507.2 dated May 31, 2010.

* cited by examiner

POLYMER SUBSTRATE WITH FLUORESCENT STRUCTURE, METHOD FOR THE PRODUCTION THEREOF AND THE USE THEREOF

CROSS-REFERENCE TO RELATED APPLICATIONS

This patent application claims the benefit of EP 09 011 507.2, filed Sep. 8, 2009, which is incorporated herein by reference.

DESCRIPTION

Figure 1:
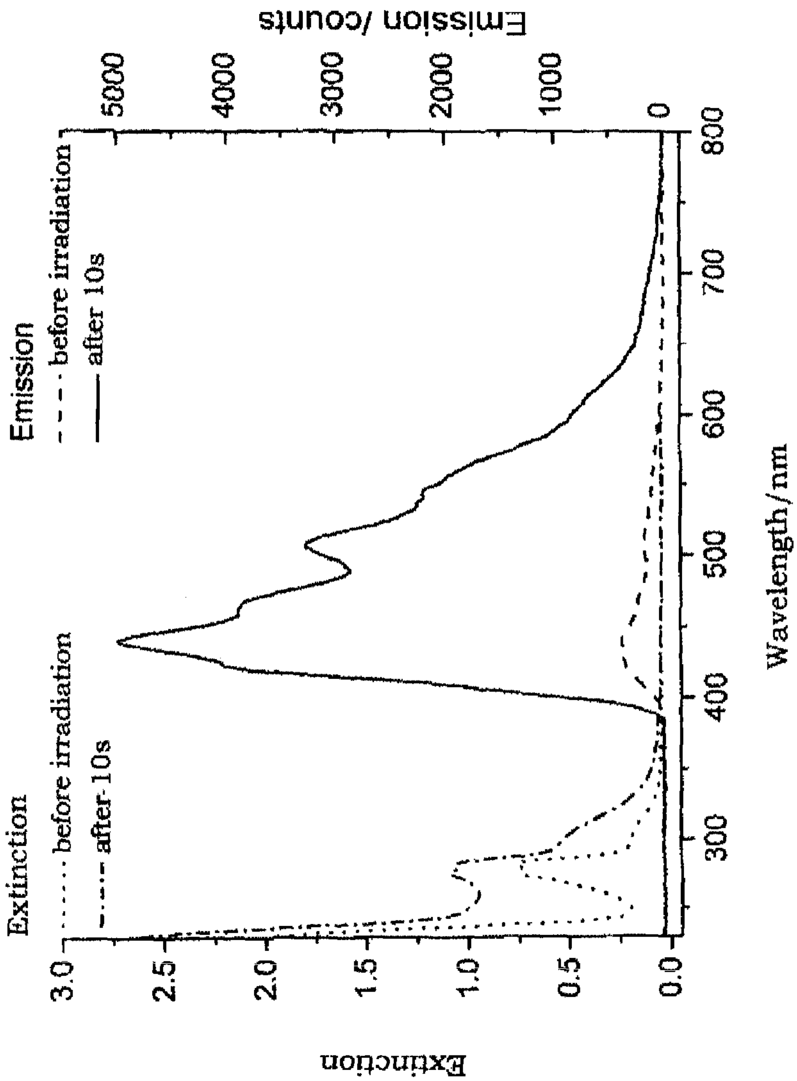
FIG. 1 depicts an emission spectrum of a polymer substrate according to the invention before and after the production of the fluorescent regions.

The invention relates to polymer substrates which are provided with fluorescence features and in which photochemical fluorescence features, i.e. fluorescent structures, are produced by UV irradiation. Thus, fluorophores can be produced in polymer substrates with a low inherent fluorescence by means of suitable UV radiation, which fluorophores display a marked and detectable emission upon being excited with light of a suitable wavelength. If such an irradiation is implemented in a structured manner, emission patterns can be produced in this way in polymer substrates, which emission patterns can be applied for example as recovery grids in fluorescence microscopy. A further application field relates to product authentication which is made possible by the polymer substrates according to the invention provided with fluorescence features.

The most varied of sampling chambers are used in the field of cultivation of cells. These are generally polymer-based and extend from the cell culture bottle via object carriers and μ slides by the company ibidi as far as multiwell plates.

These sampling chambers can have continuous surfaces on which cells grow, of 1 $mm^2$ to 100 $cm^2$. Since cells typically have a diameter of 1 μm to 30 μm, recovery of individual cells in large-area chambers without recovery structures is almost impossible.

Thus a recovery grid on a plastic material film is known from DE 100 04 135, the plastic material film being integrated in the sampling chamber. EP 2 008 715 A1 likewise describes a recovery grid which is configured as part of the plastic material body or is introduced into the plastic material body. The systems described here are based on non-fluorescent recovery grids.

A further field of the state of the art which underlies the present invention relates to the authentication of products, in particular consumer products.

The authentication of products is presently effected in the state of the art by applying fluorescent material on polymer films by means of various printing methods. Other methods for authentication of products provide that characterisation of the inherent fluorescence of polymers is effected, fluorescent dyes having been added as dopants during the production of the polymers (WO 2005/054830).

Furthermore, the fluorescence can be structured in films by an existing inherent fluorescence being bleached out.

Likewise, methods for structuring fluorescence are known, in which polymers which comprise covalently bonded precursors or to which such must be added as dopants are used.

Likewise, more complex systems which use fluorescence as a means of authentication are known, shape changes to the film combination being required however (WO 2003/101755). A further variant provides that the anisotropy of fluorescence dopants is exploited in stretched films in order to produce authentication materials (WO 2004/087795). It is common to all these methods for authentication of products that the fluorophores are distributed uniformly in the material in a planar manner so that no structured fluorescent regions are present.

Starting herefrom, it was the object of the present invention to provide polymer substrates which are provided with fluorescence features, which are simple to produce and make possible simple recognition or detection.

This object is achieved by the polymer substrate having the features and the method for the production thereof, as described herein. Methods of using the polymer substrate according to the invention also are cited. Likewise, a sampling chamber which has this polymer substrate is provided according to the invention.

The further dependent claims reveal advantageous developments.

According to the invention, a polymer substrate with a fluorescent structure is provided as integral component, a fluorescent structure being produced photochemically in regions in the polymer substrate. The preferred polymer substrates concern polymers with low inherent fluorescence, i.e. with an inherent fluorescence of the order of magnitude of a cover glass in the excitation and emission range of 200 nm to 1,000 nm. There are associated therewith in particular COC, COP, PMMA, aliphatic polyesters and polyurethanes and also polyethers. Polymers without UV stabilisers are particularly well suited. For optical microscopy, in particular polymers with a refractive index between 1.4 and 1.6, in particular with 1.51 and/or an Abbe number above 50 and/or with low double refraction are suitable.

There are thereby understood by a fluorescent structure, structures up to the optical resolution limit. However, typically structures with a lateral resolution of several μm are used. Preferably, the fluorescent structure is intended to have at least an intensity which is twice as high as the non-fluorescent structure. For standard applications, the structure should have such a high intensity that this can be detected readily even at exposure times below one second with commercially available research fluorescence microscopes. This is provided already at a factor 10.

According to the invention, the produced fluorophores which form the fluorescent structure are bonded rigidly in the polymer substrate and, with it, form a unit. The fluorescent structures are thus an integral component of the carrier. The thus modified polymer is distinguished by both the fluorescent regions and the non-fluorescent regions consisting of the identical original material. For this reason, the fluorophores can in addition also not diffuse or exude. These properties distinguish the produced structures for example significantly from an imprinted, otherwise applied structure (e.g. an impressed or lasered structure) or colourant-doped polymer systems. In addition, no possibly cell-toxic, fluorescent dyes which are applied on the polymer need be used.

According to the invention, structuring of the polymer substrate with fluorescent regions is produced. For this purpose, preferably a mask or a locally positionable radiation source is used. If the UV irradiation is undertaken in a structured manner, then only the regions which were irradiated fluoresce significantly. However, in the non-irradiated regions, no substantial increase in basic emission is achieved. In this way, patterns which are visible when excited with light of suitable wavelength can be produced. A photochemical structuring effected in this way produces regions which fluoresce in a pattern, are stable long term and stable relative to environmental influences. Furthermore, they are distinguished by not losing their edge sharpness by diffusion or similar processes. In addition, the thus produced features cannot be removed without trace.

Preferably, the fluorescent structure in the polymer substrate consists of a plurality of elements in the form of strokes, lines, symbols, figures, interference patterns or combinations hereof.

As described above, fluorescent structures with the overall extension of the pattern restricted only by the substrate size can be produced. The lateral resolution of the elements of the fluorescent structure is only restricted by the method of introduction and the light wavelength. The individual structural elements of the fluorescent patterns have however typically a lateral extension of less than 100 μm, preferably less than 10 μm.

According to the invention, a method is also provided for the production of the above-described polymer substrate, in which a polymer substrate is subjected at least in regions to irradiation in the wavelength range below 300 nm for production of fluorescent structures.

According to a variant according to the invention, the production of the fluorescent structures is thereby effected by UV irradiation using masks by imaging or contact exposure.

There are used preferably as mask for the structuring, plates which have a patterned variation of regions which are either transparent or non-transparent for the irradiation light which is used. Preferably, metallic plates which have patterned openings are used. Masks made of chromium on silica glass are particularly preferred.

As an alternative to masks for the structuring, both radiation sources with coherent (laser direct writing) and focused beam (sample positioning) can be used.

There are used as radiation sources, preferably radiation sources with emission wavelengths or emission wavelength ranges in the range below 300 nm. There are included herein in particular deuterium lamps, excimer lamps (Xe), excimer lasers ($F_2$, ArF, KrF) or solid lasers (Nd: $YVO_4$/YLF).

A polymer film is preferably used as polymer substrate.

The UV generated production of fluorophores can be tracked in the absorption spectrum of the polymer substrate by an increase in the extinction in the UV range. However, these changes do not substantially impair the optical permeability in the range of light visible to the human eye. The polymer substrates can be provided with fluorescence features without damage on the front- or rear-side. Production thereof does not require exclusion of atmospheric oxygen.

Because of a high band width of absorption and emission of the produced fluorophores, different fluorescent dyes can be generated corresponding to the excitation conditions.

The fluorescence features are distinguished furthermore by being produced directly in materials which are used in any case for products from different fields. No additional coatings, printings or other application of fluorophores, fluorescent labels or the precursors thereof are required. As a result of the fact that the features are produced directly in the material which is used, production of these relative to other methods is significantly simplified and reduced in cost. Furthermore, a completely optical process which requires no wet chemical development processes is involved.

Such emission patterns can be used in order to provide substrates for the fluorescence microscopy with a recovery grid. Typically, the recovery grids are configured as grid screen which is also provided with numbers or letters. These recovery grids facilitate recovery of specific sample areas by these being able to be characterised precisely by means of the grid screen. The recovery grids do not substantially influence biological processes and are sufficiently stable to be able to implement fairly long observations on biological and other samples with greater reliability and reproducibility.

The described, photochemically produced features are suitable, because of their absorption- and emission properties, very readily for typical excitation conditions in fluorescence microscopy, they are visible in all fluorescence channels (blue, green, yellow and red). The lateral resolution with features produced in this way is sufficiently high to enable for example a mapped observation of cells of different types.

Chambers in which such grids can be introduced are described in DE 100 04 135 A1, DE 101 05 711 A1, EP 1 458 483 A, EP 1 741 487 A1, EP 1 880 764 A1, EP 2 008 715 A1, and EP Appl. No. 09 006 487.

Essentially chambers which consist of at least an upper part and a lower part are thereby involved. The upper part thereby has at least one recess. By connection to the lower part, a reservoir is formed. According to the geometry of the recess of the upper part, the reservoir can then be configured as a closed channel/tube or as a container open at the top.

The base formed by the lower part can be a film or a coated glass carrier. The base has a preferred thickness of 50 μm to 250 μm and/or an Abbe number of greater than 50 and/or a refractive index between 1.2 and 1.8, in particular between 1.45 and 1.55. These properties are particularly suitable for (high resolution) microscopy. The base or the film can be irradiated both from the side on which the cells are intended to be cultivated subsequently and from the correspondingly opposite side in order to produce fluorescent structures. When using high-resolution microscopy techniques with a correspondingly low depth sharpness (approx. below 50 μm, typically below 10 μm), it is advantageous to fluorescence-mark the side on which the cells to be recovered will subsequently grow. As a result, the cells and the grid are situated at the same time in the optical focus, the fluorescent element being an integral component of the polymer carrier.

If the opposite side is irradiated, even already covered microfluid analysis chambers can be provided with corresponding features. Also composite films made of different materials can be used, in which at least one component has the desired properties.

In particular, also coated glass carriers can be used. Thus, for example glass cover glasses can be coated with a COP or COC layer in order then to introduce fluorescence grids into this layer via the described method. The layer can be applied for example by spin coating etc.

A further field of application relates to product authentication. Thus labels, tags and products made of polymers can be provided, by the structured UV irradiation, with a feature which is clearly visible simply by excitation with light of a suitable wavelength and intensity. In this way, security of the product against tampering is increased and a non-erasable product individualisation can be undertaken for example via barcodes. This can be achieved by a laser writing system, the feature being able also to be read electronically.

The subject according to the application is intended to be explained in more detail with reference to the subsequent Figures and examples without wishing to restrict said subject to the special embodiments shown here.

FIG. 1 shows an emission spectrum of a polymer substrate according to the invention before and after the production of the fluorescent regions. The irradiation for producing the fluorescent regions was effected here with an ArF excimer laser. The duration of the irradiation was 10 seconds. By means of the irradiation, a significant increase in the extinction in the wavelength range below 300 nm and a steep increase in the emission from 400 to 600 nm can be established.

Figure 2:
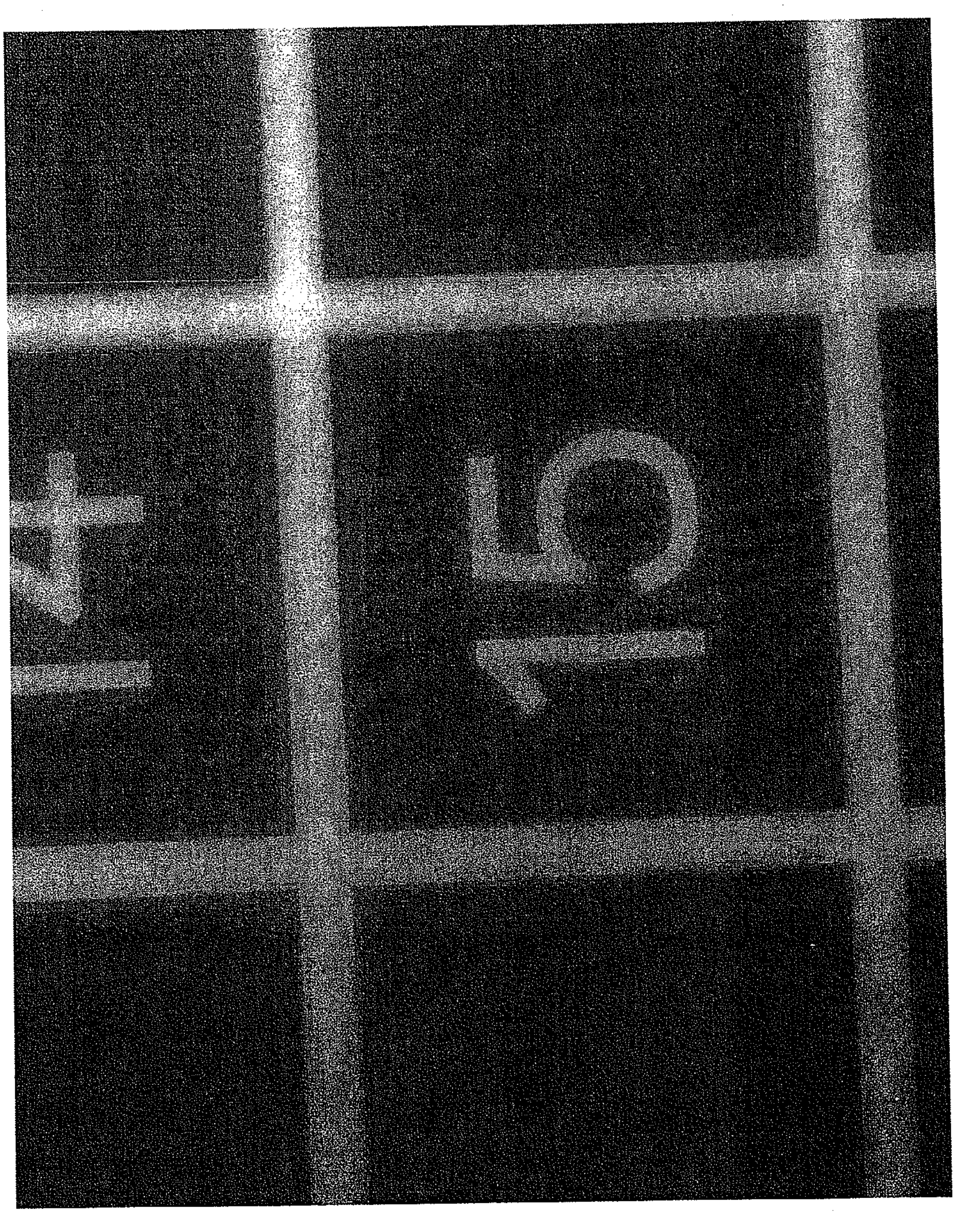
FIG. 2 represents a polymer substrate according to the invention.

A polymer substrate according to the invention is represented in FIG. 2, which polymer substrate has the number patterns which were produced with the help of a mask. A fluorescence-microscopic photograph with excitation at a wavelength of 365 nm and 200 times enlargement is hereby involved.

The following examples further illustrate the invention but, of course, should not be construed as in any way limiting its scope.

EXAMPLE 1

A mask (in a pattern, chromium on silica glass) is mounted on a COC film so that the mask is situated in one piece with the chromium side. Irradiation with a 30 W deuterium lamp is effected for 3 hours. The mask is subsequently removed and the emission pattern can be made visible by excitation at 365 nm.

EXAMPLE 2

A mask (in a pattern, chromium on silica glass) is mounted on a COC film so that the mask is situated in one piece with the chromium side. Irradiation with an ArF excimer laser (193 nm) is effected for 10 seconds. The mask is subsequently removed and the emission pattern can be made visible by excitation at 365 nm, 436 nm or 515 nm.

The invention claimed is:

1. A polymer substrate with a fluorescent structure as an integral component, wherein the fluorescent structure is produced photochemically in regions of the polymer substrate by photochemically treating regions of the polymer substrate with UV radiation, wherein the polymer substrate does not comprise a UV stabilizer, wherein the fluorescent structure of the polymer substrate has the form of a recovery grid which forms a monolithic unit with the polymer substrate and which is configured as a grid screen with numbers or letters;

wherein the polymer substrate has non-fluorescent regions; and wherein the recovery grid has an emission intensity of at least twice as high as the emission intensity of the non-fluorescent regions of the polymer substrate.

2. The polymer substrate according to claim 1, wherein the polymer substrate is selected from the group consisting of cyclic olefin copolymers (COC), cyclic olefin polymers (COP), polymethylmethacrylate (PMMA), aliphatic polyesters, polyurethanes, polyethers or composites hereof.

3. A sampling chamber comprising a polymer substrate according to claim 1.

4. The sampling chamber according to claim 3, wherein the fluorescent structure and objects/cells to be recovered are situated in one focal plane.

5. The sampling chamber according to claim 3, wherein the recovery grid and objects/cells to be recovered are spatially separated from each other in the sampling chamber.

6. The sampling chamber according to claim 3, wherein the sampling chamber has a base plate and a cover plate, a recess being provided in the base plate so that a receiving region is formed by the base plate and the cover plate, the polymer substrate being provided in the cover plate.

7. The sampling chamber according to claim 6, wherein the recess in the base plate has a base so that a cavity is formed by the cover plate.

8. The sampling chamber according to claim 7, wherein the base plate and/or cover plate has a channel opening from outside into the receiving region, in particular a through-hole.

9. The sampling chamber according to claim 6, wherein the cover plate has a thickness of from 50 μm to 250 mm.

10. The sampling chamber according to claim 6, wherein the cover plate is configured as a film.

11. The sampling chamber according to claim 10, wherein the fluorescent structure is introduced into the film.

12. A method for the production of a polymer substrate according to claim 1, in which a polymer substrate is subjected at least in regions to an irradiation in the wavelength range below 300 nm for producing fluorescent structures.

13. The method according to claim 12, wherein said fluorescent structures are produced by UV irradiation using masks by imaging or contact exposure.

14. The method according to claim 13, wherein plates with a pattern of transparent and non-transparent regions are used as masks.

15. The method according to claim 12, wherein said fluorescent structures are produced using positioning systems by irradiation with coherent or focused light.

16. The method according to claim 12, wherein, for structured production of the fluorescent structures, radiation sources with emission wavelengths or emission ranges below 300 nm are used, in particular selected from the group consisting of deuterium lamps, excimer lamps (Xe), excimer lasers (F2, ArF, KrF) or solid lasers (Nd: YVO¬ 4/YLF).

17. Labels or tags for product authentication, wherein the labels or tags comprise the polymer substrate according to claim 1.

18. Labels or tags according to claim 17, comprising fluorescence features that provide information for product authentication or/and product individualization wherein the information is encoded or unencoded.

19. The polymer substrate according to claim 1, in the form of films, blister packs or hollow bodies, as packaging elements.

20. The labels or tags according to claim 18, wherein the fluorescence features comprise information in machine-readable form.

21. The polymer substrate according to claim 1, wherein the intensity of the emission of the fluorescent regions is at least 10 times as high as the intensity of the emission of the non-fluorescent regions.

22. The sampling chamber according to claim 6, wherein the cover plate has a thickness of from 100 μm to about 200 μm.

* * * * *